United States Patent [19]

Skibbe

[11] 4,055,664

[45] Oct. 25, 1977

[54] PHARMACEUTICAL PREPARATIONS CONTAINING 4-(4-BIPHENYLYL) BUTYLAMINES AND TREATMENT OF THE ANIMAL ORGANISM THEREWITH

[75] Inventor: Martin O. Skibbe, Kankakee, Ill.

[73] Assignee: Armour Pharmaceutical Company, Phoenix, Ariz.

[21] Appl. No.: 726,081

[22] Filed: Sept. 23, 1976

Related U.S. Application Data

[62] Division of Ser. No. 548,717, Feb. 10, 1975, abandoned.

[51] Int. Cl.$^2$ ............................................. A61K 31/135
[52] U.S. Cl. ............................... 424/330; 260/570.8 R
[58] Field of Search .................. 424/330; 260/570.8 R

[56] References Cited

PUBLICATIONS

Trave et al., Chem. Abst., vol. 49, p. 2381 (1955).

Primary Examiner—Stanley J. Friedman
Attorney, Agent, or Firm—Richard R. Mybeck; Frank T. Barber

[57] ABSTRACT

Preparations containing 4-biphenylyl butylamines or pharmaceutically acceptable salts thereof and methods of using the same whereby a host, including man, to whom such preparations are administered, is provided with anti-inflammatory, antipyretic and analgesic relief while avoiding the unwanted side effects of steroid therapy.

The preparations of this invention contain compounds having the structure

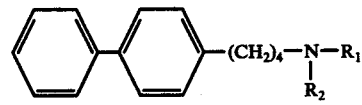

wherein: $R_1$ is selected from the group consisting of hydrogen and lower alkyls having from one to four carbon atoms; and $R_2$ is selected from the group consisting of hydrogen and lower alkyls having from one to four carbon atoms. The pharmaceutically acceptable salts are formed on the same basis structure as shown.

15 Claims, No Drawings

PHARMACEUTICAL PREPARATIONS CONTAINING 4-(4-BIPHENYLYL) BUTYLAMINES AND TREATMENT OF THE ANIMAL ORGANISM THEREWITH

This is a divisional application from copending application U.S. Ser. No. 548,717 filed Feb. 10, 1975, now abandoned.

This invention relates to pharmaceutical preparations and their use and more particularly to the unexpected benefits obtained when a preparation containing certain 4-biphenylyl butylamines or pharmaceutically acceptable salts thereof are administered to a host afflicted with a condition requiring anti-inflammatory, antipyretic or analgesic relief.

The properties of these compounds and especially their lack of any significant side effects, makes them a highly valuable discovery since, as used, they provide relief for patients who, suffering from inflammatory conditions, cannot tolerate steroid therapy in the treatment thereof.

The therapeutically active compounds of this invention have the structural formula:

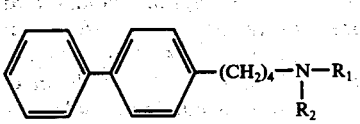

wherein: $R_1$ is selected from the group consisting of hydrogen and lower alkyls having from one to four carbon atoms; and $R_2$ is selected from the group consisting of hydrogen, and lower alkyls having from one to four carbon atoms.

Representative of compounds useful in the preparations and methods of the present invention are:
4-(4-biphenyl)-butylamine;
4-(4-biphenylyl)-N-methyl-butylamine;
4-(4-biphenylyl)-N-ethyl-butylamine;
4-(4-biphenylyl)-N-propyl-butylamine;
4-(4-biphenylyl)-N-butyl-butylamine;
4-(4-biphenylyl)-N,N-diethyl-butylamine;
4-(4-biphenylyl)-butylamine; and the non-toxic acid addition salts of each of the foregoing.

Our entire group of compounds, for ease of expression, shall, from time to time, herein be referred to as "4-biphenylyl butylamines and selected derivatives thereof" even though in certain instances the more correct nomenclature should be "4-(4-biphenylyl)-butylamines". The beneficial effects obtained when these compounds are formulated into pharmaceutically acceptable dosage forms and administered to a host requiring anti-inflammatory, antipyretic or analgesic therapy is new and totally unexpected.

Thus, the present invention is predicated upon our discovery that beneficial effects are obtainable when 4-biphenylyl butylamines and selected derivatives thereof are employed in pharmaceutically acceptable forms to effectively disseminate the compound within the host to which it is administered to the benefit of the host.

"Inflammatory conditions", as that term is used herein, refers to those physical conditions exhibiting one or more of the symptoms, redness, pain, heat and swelling. In the past, inflammatory conditions have been treated with various analgesics, antipyretics, narcotics, hormones, and steroids, alone or in combination. In some inflammatory conditions, such as the rheumatoid diseases, particularly rheumatoid arthritis, the generally accepted approach has been treatment by the administration of adrenocorticosteroids, if and when the subject can assimilate and tolerate the drug. However, extreme care must be exercised in administering steroids so as to avoid or minimize the various undesirable side effects which, as is well known in the art, are frequently encountered with such drugs.

"Antipyretic conditions", as that term is used herein, refers to those physical conditions exhibiting heat, either locally or as fever. Conditions to which the analgesic properties are directed will usually involve pain.

The present invention is based upon our discovery of the remarkably unexpected anti-inflammatory, antipyretic and analgesic action obtained when preparations containing 4-biphenylyl butylamines or selected derivatives thereof, as herein defined, are administered to a host having an inflammatory, pyretic or painful condition. For convenience, all of such indications will be referred to as "inflammatory conditions".

Accordingly, a prime object of the present invention is to provide a new and useful pharmaceutical preparation containing as its principal active ingredient, the compound 4-biphenylyl amine or selected derivatives thereof.

Another object of the present invention is to provide a new pharmaceutical preparation which is a potent anti-inflammatory agent.

A further object of the present invention is to provide an anti-inflammatory agent which substantially precludes the nervous side effects accompanying exogenous steroid therapy of inflammatory conditions.

These and still further objects as shall hereinafter appear are fulfilled by the present invention in a remarkably unexpected manner as will be readily discerned from a careful consideration of the following detailed description of exemplary embodiments thereof.

In one practice of the present invention, 4-(4-biphenylyl) butylamine is prepared by the admixture of a solution of 4-(4-biphenylyl)-butyramide and tetrahydrofuran to a mixture of lithium aluminum hydride and ether. The admixture is refluxed for about 24 hours, decomposed with water and provided with an alkaline pH (i.e., > 7) by the addition of sodium hydroxide in water. The organic portion is then evaporated to leave the free amine. The free amine can be utilized in that form or it may be further reacted with an acid to form a non-toxic salt.

Of course, in the foregoing procedure, the 4-(4-biphenylyl) butylamine is described as illustrative only and the procedure can be followed to prepare the other derivatives herein described using the appropriate starting material.

The finished compound may thereafter be formulated into pharmaceutical unit dosage forms using the known procedures of mixing, granulating, compressing, suspending or dissolving and adding suitable pharmaceutical carriers or non-toxic excipients thereto.

In one embodiment of our invention, the principal active ingredient of our pharmaceutical preparation is 4-(4-biphenylyl) butylamine, as herein defined, or a pharmaceutically acceptable salt thereof, e.g., a non-toxic salt of sulfuric, nitric, phosphoric, citric, acetic, lactic, tartaric, sulfamic, succinic, fumaric, maleic, ethanedisulfonic, hydrobromic, benzoic or a similar acid. The acceptable salts may be formed by reacting the amine base with excess acid in a suitable solvent such as ethanol, ether, acetone, water or mixtures thereof. The mixture is heated to facilitate solution and the salts crystallize therefrom on cooling.

The preferred dosage forms for this invention contain our principal active ingredients associated with an acceptable pharmaceutical carrier. The carrier, a non-toxic pharmaceutical grade substance, may be either solid or liquid. Suitable flavors or sweeteners may also be added, if desired, to those forms for oral administration. The routes by which our preparation may be administered are subcutaneous, intramuscular and intravenous injection; pancaval insertion, including oral; and topical application.

Suitable solid carriers for use herewith include lactose, magnesium stearate, starch, sucrose, mannitol, sorbitol, cellulose powder, dicalcium phosphate, talc, stearic acid, gelatin, agar, pectin, acacia and the like.

Suitable liquid carriers include glycols, polyglycols, peanut oil, olive oil, sesame oil, alcohols, sterile water and the like. If desired, the carrier may include a time delay material such as glycerol monostearate, shellac or glycerol distearate, either alone or with wax. Microencapsulation can also be used when desired.

Our composition preferably is provided in unit dosage forms for accuracy and convenience in administration. When appropriate, oral administration is effective and preferred and dosage units suitable for oral administration are provided. Such dosage forms which employ solid carriers include tablets, filled capsules, packets, lozenges, troches and the like. The amount of solid carrier per dosage unit may vary widely, e.g., from 25 mg to 1 gram, depending upon the form selected. The choice of an appropriate amount is well within the skill of an artisan once confronted with this disclosure.

Our 4-biphenylyl butylamines and selected derivatives thereof may also be compounded with semi-solid and liquid carriers in solutions, suspensions, emulsions, ointments, suppositories and soft gelatin capsules, for example. Such compositions may be administered pancavally, e.g., via natural and artificial openings in the body such as the mouth, the anus, the vagina, the nares, and the stoma of colostomy patients; intravenously; intramuscularly; or topically, employing the appropriate composition having a suitable concentration of active ingredient according to the desired route of administration.

An inflammatory condition is treated in accordance with the invention by administering the preparation of this invention in an amount sufficient to alleviate the symptoms of the condition. The compound will be administered at a daily dosage of from 25 mg to 2,000 mg of the active ingredient disposed in a pharmaceutical carrier. A preferred daily amount of from 100 to 1,000 mg of the drug gives satisfactory results when oral administration is desired. When routes of administration such as topical and intramuscular are desired, the dosage level may be substantially reduced.

The dosage level, and frequency of administration will vary to a great extent between conditions and between patients. It is, therefore, required that the physician take into consideration the cause of the condition, the case history of the patient, the reaction of the subject, the preferred route of administration, and like parameters in prescribing dosages. The daily dosage may be administered during one or more times during the day. Tablets and gelatin capsules are especially well suited when oral administration is selected for the practice of this invention.

To further aid in the appreciation and comprehension of the present invention, and not to limit its scope, the following examples are presented.

EXAMPLE I

A solution of 6.0 g. (0.025 mole) 4-(4-biphenylyl)-butyramide in 250 ml. tetrahydrofuran was added to a mixture of 0.95 g. (0.025 mole) lithium aluminum hydride and 100 ml. ether. The mixture was refluxed for 24 hours, decomposed with 25 ml. water, and made basic by the addition of 6 g. sodium hydroxide in 15 ml. water. Evaporation of the organic portion furnished the free amine; namely, 4-(4-biphenylyl) butylamine.

EXAMPLE II 4-(4-biphenylyl) butylamine prepared according to the procedure of Example I is treated with ydrochloric acid. The hydrochloride was then isolated and provided a yield of 4.2 g. (64.3%), m.p. 262°–264° C.

Analysis: Calculated for $C_{16}H_{20}ClN$: C, 73.39; H, 7.71; N, 5.35. Found: C, 73.43; H, 7.77; N, 5.19.

EXAMPLE III 4-(4-biphenylyl)-N-methyl-butylamine hydrochloride was prepared using the procedure of Example I; namely, the reduction of 4-(4-biphenylyl)-N-methyl-butyramide (m.p. 132°–134° C.) with an equal molar concentration of lithium aluminum hydride in a solution of tetrahydrofuran. The amine thus formed was converted to the hydrochloride by the addition of hydrochloric acid. A yield of 72.5% was obtained having an m.p. of 223°–225° C.

Analysis: Calculated for $C_{17}H_{22}ClN$: C, 74.01; H, 8.05; N, 5.08 Found: C, 74.02; H, 7.99; N, 4.82.

EXAMPLE IV 4-(4-biphenylyl)-N-methyl-butylamine was prepared by the procedure of Example III, omitting the hydrochloride conversion step.

EXAMPLE V 4-(4-biphenylyl)-N-ethyl-butylamine was prepared by the procedure of Example IV except that 4-(4-biphenylyl)-N-ethyl butyramide (m.p. 126°–128° C.) was used as the starting material. A yield of 64.0% having an m.p. of 233°–235° C. was obtained.

EXAMPLE VI 4-(4-biphenylyl)-N-ethyl-butylamine hydrochloride was prepared by reacting the product obtained by Example V with hydrochloric acid.

Analysis: Calculated for $C_{18}H_{24}ClN$: C, 74.57; H, 8.36; N, 4.83. Found: C, 74.67; H, 8.41; N, 4.71.

EXAMPLE VII 4-(4-biphenylyl)-N,N-diethyl-butylamine was prepared by the procedure of Example IV except that 4-(4-biphenylyl)-N,N-diethyl-butyramide (b.p. 181.3° C. — 10.05 mm) is also convertible to a non-toxic acid addition salt by reaction with a suitable acid such as hydrochloric acid. A yield of 63.8% was obtained having an m.p. of 133.4° C.

Analysis: Calculated for $C_{20}H_{28}ClN$: C, 75.55; H 8.89; N, 4.41. Found: C, 75.68; H, 8.85; N, 4.25.

EXAMPLE VIII

The butyramides used in the foregoing examples were prepared by reacting 4-(4-biphenylyl) butyryl chloride (m.p. 41°-42° C.) with an alkyl or dialkyl amine such as methylamine, ethylamine, propylamine, dimethylamine and the like according to the reaction:

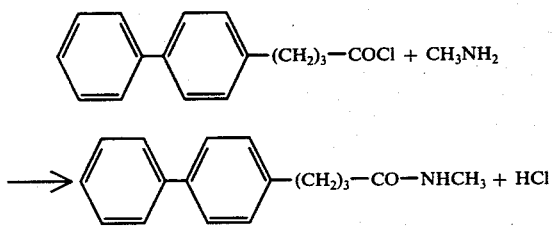

EXAMPLE IX

Several dosage forms were prepared embodying the present invention. They are shown as Compositions A through K below, with the notation "active ingredient" signifying a compound of this invention and including the non-toxic pharmaceutically active salts thereof.

COMPOSITION A

Tablets suitable for oral administration and having the following composition per tablet are produced by compounding the ingredients in the same relative proportions:

| Ingredients | Amount m.g. |
|---|---|
| Active ingredient | 200 |
| Sorbitol | 15 |
| Mannitol | 85 |
| Gelatin as a 10% aqueous solution | 6 |
| Corn starch | 30 |
| Magnesium stearate | 4 |

The first three ingredients are milled together to a uniform powder and granulated into the gelatin solution. The mixture is screened onto trays and dried at 60° C. The dried granules are sized, mixed with the corn starch and the magnesium stearate, and compressed into tablets.

COMPOSITION B

Tablets suitable for oral administration and having the following composition per tablet are produced by compounding the ingredients in the same relative proportions:

| Ingredients | Amount m.g. |
|---|---|
| Active ingredient | 200 |
| Microcrystalline cellulose[1] | 150 |
| Polyvinyl pyrrolidone | 5 |
| Magnesium stearate | 4 |

[1]Avicel (FMC Corporation, U.S. Pat. No. 2,978,446), average particle size 38 microns.

The first three ingredients are mixed to uniformity and lubricated with a portion of the magnesium stearate. The mixture is compressed into slugs, and the slugs are granulated. The granules are lubricated with the remainder of the magnesium stearate and compressed into tablets.

COMPOSITION C

Filled gelatin capsules suitable for oral administration and containing the following composition in each capsule are produced by compounding the ingredients in the same relative proportions:

| Ingredients | Amount m.g. |
|---|---|
| Active ingredient | 200 |
| Lactose | 175 |
| Magnesium stearate | 5 |

The above ingredients are screened through a #40 U.S. mesh screen to a uniform powder, transferred to a mixer, mixed well, and filled into No. 1 hard gelatin capsules.

COMPOSITION D

Filled soft gelatin capsules suitable for oral administration and containing the following composition in each capsule are produced by compounding the ingredients in the same relative proportions:

| Ingredients | Amount m.g. |
|---|---|
| Active ingredient | 50 |
| Sesame oil | 50 |

The ingredients are mixed to form a thick slurry, and the slurry is filled into soft gelatin capsules.

COMPOSITION E

Filled soft gelatin capsules suitable for oral administration and containing the following composition in each capsule are produced by compounding the ingredients in the same relative proportions:

| Ingredients | Amount m.g. |
|---|---|
| Active ingredient | 300 |
| Polyethylene glycol 400 | 240 |

The ingredients are mixed to form a thick slurry, and the slurry is filled into soft gelatin capsules.

COMPOSITION F

Tablets used for oral administration and having the following composition per tablet are produced by compounding the ingredients in the same relative proportions:

| Ingredients | Amount m.g. |
|---|---|
| Active ingredient | 200 |
| Dicalcium phosphate | 180 |
| Corn starch | 60 |
| Polyvinylpyrrolidone | 5 |
| Magnesium stearate | 4 |

The active ingredient, dicalcium phosphate and a portion of the starch and magnesium stearate are mixed, granulated with an alcoholic solution of the polyvinylpyrrolidone, dried, and sized. The remainder of the starch and the magnesium stearate are added and mixed. This mixture then is compressed into tablets.

COMPOSITION G

Tablets used for oral administration and having the following composition per tablet are produced by compounding the ingredients in the same relative proportions:

| Ingredients | Amount m.g. |
|---|---|
| Active ingredient | 200 |
| Lactose | 200 |
| Microcrystalline cellulose | 30 |
| Polyvinylpyrrolidone | 5 |
| Amberlite XE-88[1] | 5 |
| Magnesium stearate | 4 |

[1]Potassium salt of a carboxylic acid cation exchange resin available at Rohm & Haas, Philadelphia, Pa.

COMPOSITION H

Tablets useful for oral administration and having the following composition per tablet are produced by compounding the ingredients in the relative proportions indicated:

| Ingredients | Amount m.g. |
|---|---|
| Active ingredient | 50 |
| Microcrystalline cellulose | 79 |
| Magnesium stearate | 1 |

Tablets may be white or colored with appropriate food, drug and cosmetic or drug and cosmetic dyes.

COMPOSITION I

The following ingredients are compounded to provide a solution suitable for intramuscular administration:

| Ingredients | Amount g. |
|---|---|
| Active ingredient | 20 |
| Polyethylene glycol 200, q.s. up to 1 liter | |

The ingredients are mixed and warmed to about 50°–60° C. with stirring to effect solution. The solution is sterile filtered, cooled to room temperature and packaged in sterile vials.

COMPOSITION J

Suppositories melting at about 60° F. and each having the following composition are produced by compounding the ingredients in the same relative proportions:

| Ingredients | Amount m.g. |
|---|---|
| Active ingredient | 200 |
| Polyethylene glycol 600 | 200 |
| Polyethylene glycol 4000 | 800 |

The ingredients are mixed and heated to about 60° C. to effect solution. The solution is poured into cooled molds and allowed to cool and solidify.

COMPOSITION K

An ointment suitable for topical administration has the following composition, in parts by weight:

| Ingredients | Amount |
|---|---|
| Active ingredient | 200 |
| Polyethylene glycol 1540 | 500 |
| Polyethylene glycol 4000 | 80 |

-continued

| Ingredients | Amount |
|---|---|
| Propylene glycol | 200 |
| Cetyl alcohol | 20 |

The polyethylene glycols and cetyl alcohol are mixed and warmed to about 60° C. The active triazine ingredient then is stirred into the mixture to effect solution. The propylene glycol is added to the solution with strring until cool. The cool ointment is filled into jars.

EXAMPLE X

Selected compounds of this invention were tested for anti-inflammatory activity using the carrageenin edema test described by Winter et al. (Proc. Soc. Exp. Biol. Med., 111,544 (1962)).

The compounds were administered in pectin suspension by gavage at a dosage of 100 mg./kg. to adult male Holtzman rats 1 hour before injection of 0.05 ml. of 1% suspension of carrageenin in sterile 0.9% sodium chloride solution into the plantar tissue of the right hand paw. Each drug was administered to a group of 6 rats. The volume of the injected foot was measured immediately and then again 3 hours later. The average increase in volume was calculated and compared with that of control animals which received pectin only before injection with 0.05 ml. of the 1% carrageenin suspension. The percent inhibition was then calculated for each drug. The value of 20% or greater is indicative of anti-inflammatory activity in this assay.

Phenylbutazone was used as the standard for comparison.

Representative compounds used in this assay and in the assays of Examples XII and XIII are coded as follows:

| Code | Compound |
|---|---|
| A | 4-(4-biphenylyl)-butylamine hydrochloride |
| B | 4-(4-biphenylyl)-N-methyl-butylamine hydrochloride |
| C | 4-(4-biphenylyl)-N-ethyl-butylamine hydrochloride |
| D | 4-(4-biphenylyl)-N,N-diethyl-butylamine |
| E | 4-(4-biphenylyl)-N,N-diethyl-butylamine hydrochloride |

The results of the Carrageenin-edema anti-inflammatory assay are reported in Table I.

TABLE I

| | Percent Inhibition 1 Hr. Pretreatment | | |
|---|---|---|---|
| Compound | 100 mg. | 31.6 mg. | 10.0 mg. |
| A | 52 | — | 38 |
| B | 31 | — | — |
| C | 24 | — | — |
| D | 32,41 | 22 | 10 |
| E | 17 | — | — |
| Phenylbutazone | 47 | 50 | 36 |

EXAMPLE XI

Selected compounds prepared according to this invention were pharmacologically tested in rats using the antipyretic assay. The rats used were Holtzman males (180–220 grams).

In this assay pyresis is induced in rats (five per group) by the subcutaneous injection of a 16 percent yeast suspension. Drugs are administered orally sixteen hours later and rectal temperatures (degrees Fahrenheit) recorded hourly for the subsequent six hours. Each value in Table II is the mean temperature decrease of these six hourly readings as compared to vehicle treated control rats. Phenylbutazone is used as a standard for comparison.

TABLE II

| Compound | Temperature Drop. ° F. | | |
|---|---|---|---|
| | 100 mg. | 31.6 mg. | 10.0 mg./Kg. |
| A | 3.6 | 3.3 | 2.6 |
| B | — | — | — |
| C | — | — | — |
| D | 0.8 | 0 | 0 |
| E | — | — | — |
| Phenylbutazone | 2.7 | 2.7 | 1.1 |

The Antipyretic Test used above is described by Winder, C. V., Wax, J., Serrano, B., Scott, L., Stackhouse, S. P. and Wheelock, R. H., Pharmacological Studies of 1,2-dimethyl-3-phenyl-3-propionoxypyrolidine (CI-427) An Analgesic Agent - Journal of Pharmacology and Experimental Therapeutics, Vol. 133, pages 117–128 (1961).

EXAMPLE XII

Selected compounds prepared according to this invention were pharmacologically tested in mice (Carworth Farms C.F.E. females, 17-22 grams) using the Writhing Response Test described by Pearl, J. and Harris, L. S., Inhibition of Writhing by Narcotic Antagonists - Journal of Pharmacology and Experimental Therapeutics, Vol. 154, pages 319–323 (1966).

In this test mice that have been fasted for six hours are injected i.p. with an 0.6% v/v solution of acetic acid. After five minutes the number of writhings is measured for a period of five minutes. Drugs are administered orally in a 1% pectin suspension one hour prior to the test. Values shown in Table III are precent inhibition of drug tested versus control groups. Aminopyrine is used as a standard for comparison.

TABLE III

| Compound | Percent Inhibition Dose | | | |
|---|---|---|---|---|
| | 20 mg. | 50 mg. | 100 mg. | 200 mg./Kg. |
| A | 27 | 46 | 75 | 80 |
| B | — | — | — | — |
| C | — | — | — | — |
| D | 25 | 39 | 69 | 88 |
| E | 5 | 26 | 62 | 74 |
| Aminopyrine | 42 | 74 | 89 | 93 |

From the foregoing, it becomes apparent that new and quite remarkable pharmaceutical preparations have been herein described and illustrated which have the surprising ability when administered to a host to relieve inflammatory conditions while avoiding steroid side effects. It is, of course, understood that the artisan confronted with this disclosure will contemplate various alterations, modifications and applications, all of which are intended to be encompassed within the spirit of this invention, especially as it is defined by the scope of the claims appended hereto.

What is claimed is:

1. A pharmaceutical preparation in unit dosage form selected from the group consisting of a tablet, a filled capsule, a packet, a lozenge, a troche, a solution, a suspension, an emulsion, an ointment, a suppository and a soft gelatin capsule and having, when administered to a host with an inflammatory condition, an anti-inflammatory activity, said preparation comprising a pharmaceutically acceptable carrier and from about 1 mg. to about 2,000 mg. of a member selected from the group consisting of a 4-(4-biphenylyl) butylamine compound having the structure shown below and a non-toxic pharmaceutically acceptable acid salt thereof, said structure being

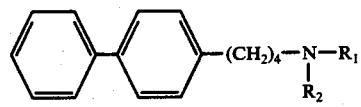

wherein: $R_1$ is selected from the group consisting of hydrogen and a lower alkyl having from one to four carbon atoms; and $R_2$ is selected from the group consisting of hydrogen, and a lower alkyl having from one to four carbon atoms.

2. A preparation according to claim 1 containing from about 50 mg. to about 1,000 mg. of said compound or its non-toxic pharmaceutically acceptable acid salt and adapted for administration by a route selected from the group consisting of intramuscular, intravenous, subcutaneous, and pancaval, including oral.

3. A preparation according to claim 1 in which said compound is 4-(4-biphenylyl)-butylamine hydrochloride.

4. A preparation according to claim 1 in which said compound is 4-(4-biphenylyl)-N-methyl-butylamine hydrochloride.

5. A preparation according to claim 1 in which said compound is 4-(4-biphenylyl)-N-ethyl butylamine hydrochloride.

6. A preparation according to claim 1 in which said compound is 4-(4-biphenylyl)-N,N-diethyl-butylamine.

7. A preparation according to claim 1 in which said compound is 4-(4-biphenylyl)-N,N-diethyl-butylamine hydrochloride.

8. The method of treating an inflammatory condition of a host, including man, comprising administering to said host daily from about 1 mg. to about 2,000 mg. of a compound having the structure

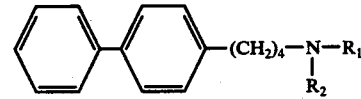

wherein: $R_1$ is selected from the group consisting of hydrogen and a lower alkyl having from one to four carbon atoms; and $R_2$ is selected from the group consisting of hydrogen, and a lower alkyl having from one to four carbon atoms.

9. The method of claim 8 in which said compound is administered subcutaneously, pancavally, intramuscularly or intravenously in an amount of from about 50 mg. to about 1,000 mg. per day.

10. The method of claim 8 in which said compound is administered topically in an amount of at least 1 mg. per day.

11. The method of claim 8 in which said compound is 4-(4-biphenylyl)-butylamine hydrochloride.

12. The method of claim 8 in which said compound is 4-(4-biphenylyl)-N-methyl-butylamine hydrochloride.

13. The method of claim 8 in which said compound is 4-(4-biphenylyl)-N-ethyl-butylamine hydrochloride.

14. The method of claim 8 in which said compound is 4-(4-biphenylyl)-N,N-diethyl-butylamine.

15. The method of claim 8 in which said compound is 4-(4-biphenylyl)-N,N-diethyl-butylamine hydrochloride.

* * * * *